US006753454B1

(12) United States Patent
Smith et al.

(10) Patent No.: US 6,753,454 B1
(45) Date of Patent: Jun. 22, 2004

(54) ELECTROSPUN FIBERS AND AN APPARATUS THEREFOR

(75) Inventors: Daniel J. Smith, Stow, OH (US); Darrell H. Reneker, Akron, OH (US); Albert T. McManus, San Antonio, TX (US); Heidi L. Schreuder-Gibson, Holliston, MA (US); Charlene Mello, Rochester, MA (US); Michael S. Sennett, Sudbury, MA (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 09/571,841

(22) Filed: May 16, 2000

Related U.S. Application Data
(60) Provisional application No. 60/158,677, filed on Oct. 8, 1999.

(51) Int. Cl.[7] .............................................. A61F 13/00
(52) U.S. Cl. ............................ 602/41; 602/42; 602/43; 602/45
(58) Field of Search ..................................... 602/41–47

(56) References Cited

U.S. PATENT DOCUMENTS

| | | | |
|---|---|---|---|
| 4,043,331 A | 8/1977 | Martin et al. ................ 128/156 |
| 4,323,525 A | 4/1982 | Bornat ......................... 264/24 |
| 4,345,414 A | 8/1982 | Bornat et al. ................ 53/425 |
| 4,565,736 A | 1/1986 | Stein et al. .................. 428/286 |
| 4,657,793 A | 4/1987 | Fisher ......................... 428/36 |
| 4,788,016 A | 11/1988 | Colclough et al. ............ 264/10 |
| 4,795,330 A | 1/1989 | Noakes et al. ................ 425/6 |
| 4,815,457 A | * | 3/1989 | Mazars et al. ................ 602/57 |
| 4,829,996 A | 5/1989 | Noakes et al. ........ 128/200.14 |
| 4,878,908 A | 11/1989 | Martin et al. .................. 623/1 |
| 5,300,192 A | * | 4/1994 | Hansen et al. .............. 162/184 |
| 5,512,291 A | 4/1996 | Li ................................ 424/443 |
| 5,522,879 A | 6/1996 | Scopelianos .................... 623/1 |
| 5,639,467 A | 6/1997 | Dorian et al. ................ 424/422 |
| 5,655,517 A | 8/1997 | Coffee .................... 128/203.12 |
| 5,656,468 A | 8/1997 | Dorian et al. ................ 435/178 |
| 5,670,557 A | * | 9/1997 | Dietz et al. .................. 522/184 |
| 5,813,614 A | 9/1998 | Coffee ......................... 239/690 |
| 5,915,377 A | 6/1999 | Coffee .................... 128/200.16 |

FOREIGN PATENT DOCUMENTS

| | | | |
|---|---|---|---|
| EP | 0 250 102 | 12/1987 | ............. B05B/5/02 |
| EP | 0 303 496 A | 12/1988 | ........... A61L/31/00 |
| WO | WO 98/03267 | 1/1998 | ........... B05B/5/025 |

OTHER PUBLICATIONS

Y.A. Dzenis and D. H. Reneker *Polymer Hybrid Nano/Micro Composites* Proceedings of the American Society for Composites—Ninth Technical Conference, 1994, pps.657–665 XP–000978395.

Joseph A. Bauer, Weisun Rao, and Daniel J. Smith *Evaluation of Linear Polyethylenimine/Nitric Oxide Adduct on Wound Repair: Therapy versus Toxicity* Wound Repair and Regeneration, vol. 6, No. 6, Nov. 1998 pps.569–577, XP000978321 ISSN: 10667–1927.

* cited by examiner

*Primary Examiner*—Nicholas D. Lucchesi
*Assistant Examiner*—Lalita M Hamilton
(74) *Attorney, Agent, or Firm*—Roetzel & Andress (57) ABSTRACT

A novel fiber comprising a substantially homogeneous mixture of a hydrophilic polymer and a polymer which is at least weakly hydrophobic is disclosed. The fiber optionally contains a pH adjusting compound. A method of making the fiber comprises electrospinning fibers of the substantially homogeneous polymer solution. A method of treating a wound or other area of a patient requiring protection from contamination comprises electrospinning the substantially homogeneous polymer solution to form a dressing. An apparatus for electrospinning a wound dressing is discosed.

17 Claims, 5 Drawing Sheets

ELECTROSPUN FIBERS AND AN APPARATUS THEREFOR

This application claims benefit of pending U.S. Provisional Application No. 06/158,677 filed on Oct. 8, 1999.

TECHNICAL FIELD

This invention relates to an article of manufacture comprising electrospun fibers. More particularly, this invention relates to composite nanofibers that can be produced by electrospinning polymeric matrix material. Even more particularly, this invention relates to a non-woven nanofiber composite that possesses improved qualities regarding strength, absorbency, and pH adjustability. This invention also relates to an apparatus for electrospinning the fibers. The apparatus of the present invention allows for the application of fibers to a specific target. The apparatus also allows for the application of fibers containing a wider range of potential performance enhancing additives than was previously believed possible.

BACKGROUND OF THE INVENTION

The technique of electrospinning, also known within the fiber forming industry as electrostatic spinning, of liquids and/or solutions capable of forming fibers, is well known and has been described in a number of patents as well as in the general literature.

The process of electrospinning generally involves the creation of an electrical field at the surface of a liquid. The resulting electrical forces create a jet of liquid which carries electrical charge. Thus, the liquid jets maybe attracted to other electrically charged objects at a suitable electrical potential. As the jet of liquid elongates and travels, it will harden and dry. The hardening and drying of the elongated jet of liquid may be caused by cooling of the liquid, i.e., where the liquid is normally a solid at room temperature; evaporation of a solvent, e.g., by dehydration, (physically induced hardening); or by a curing mechanism (chemically induced hardening). The produced fibers are collected on a suitably located, oppositely charged receiver and subsequently removed from it as needed, or directly applied to an oppositely charged generalized target area.

Fibers produced by this process have been used in a wide variety of applications, and are known, from U.S. Pat. Nos. 4,043,331 and 4,878,908, to be particularly useful in forming non-woven mats suitable for use in wound dressings. One of the major advantages of using electrospun fibers in wound dressings, is that very thin fibers can be produced having diameters, usually on the order of about 50 nanometers to about 25 microns, and more preferably, on the order of about 50 nanometers to about 5 microns. These fibers can be collected and formed into non-woven mats of any desired shape and thickness. It will be appreciated that, because of the very small diameter of the fibers, a mat with very small interstices and high surface area per unit mass, two characteristics that are important in determining the porosity of the mat, can be produced.

Wound dressings formed using non-woven mats of these polymeric fibers may provide particular benefits depending upon the type of polymer or polymers used. A wettable, or hydrophilic, polymer, such as, for example, a polyurethane may be used, or a non-wetting, or at least weakly hydrophobic, polymer such as, for example, a saturated polyester, may be employed. Where the dressing is formed from a wettable polymer, blood or serum escaping from the wound tends to penetrate the dressing and the high surface area encourages clotting. Such dressings could be used as emergency dressings to halt bleeding. On the other hand, where the dressing is formed from a non-wetting polymer, and if the interstices between the fibers are sufficiently small, i.e., on the order of less than about 100 microns, tissue fluids, including blood, tend not to permeate the dressing. Consequently, the fluids are retained adjacent to the wound where clotting will occur. Subsequent removal of such a dressing is facilitated by the absence of blood clots permeating the dressing material. Still further, U.S. Pat. Nos. 4,043,331 and 4,878,908 suggest that such dressings have the advantage that they are usually sufficiently porous to allow interchange of oxygen and water vapor between the atmosphere and the surface of the wound.

Besides providing variability as to the diameter of the fibers or the shape, thickness, or porosity of any non-woven mat produced therefrom, the ability to electrospin the fibers also allows for variability in the composition of the fibers, their density of deposition and their inherent strength. The above-identified U.S. patents indicate that it is also possible to post-treat the non-woven mats with other materials to modify their properties. For example, one could increase the strength of the mat using an appropriate binder or increase water resistance by post-treating the mat with silicone or other water-resistant material.

By varying the composition of the fibers being electrospun, it will be appreciated that fibers having different physical or chemical properties may be obtained. This can be accomplished either by spinning a liquid containing a plurality of components, each of which may contribute a desired characteristic to the finished product, or by simultaneously spinning, from multiple liquid sources, fibers of different compositions that are then simultaneously deposited to form a mat. The resulting mat, of course, would consist of intimately intermingled fibers of different material. A further alternative noted in the U.S. patents is to produce a mat having a plurality of layers of different fibers of different materials (or fibers of the same material but different characteristics, e.g. diameter), as by, for example, varying the type of fibers being deposited on the receiver over time. For example, wettable and non-wetting polymers each offer additional properties that may be desirable in different applications. Wettable polymers tend to be highly absorbant but are relatively weak, while non-wetting polymers tend to be non-absorbant but relatively strong. In some applications, such as medical dressings, for example, it may be desirable to use a combination of wettable and non-wetting polymer layers in a single article. In such an application, the wettable polymer layer or layers contribute a relatively high level of absorbency to the article while the non-wetting polymer layer or layers contribute a relatively high level of strength. Use of such a laminate-type structure, however, suffers from the disadvantage that the hydrophobic layer can form a barrier to liquids and interfere with the absorption of liquid by the wettable layer. Additionally, upon absorption of liquid, the wettable polymer layer will lose its three dimensional structure, and misalignment, slipping, or even separation of the layers may occur, resulting in failure of the integrity of the article.

Thus, U.S. Pat. Nos. 4,043,331 and 4,878,908 make it clear that strong, non- woven mats comprising a plurality of fibers of organic, namely polymeric, material produced by electrostatically spinning the fibers from a liquid consisting of the material or precursor thereof is known in the art. These fibers are collected on a suitably charged receiver and subsequently removed therefrom. The mats or linings then formed on the receiver can then be transferred and used in conjunction with other previously constructed components such as, for example, mats of woven fibers and backing layers to provide a wound dressing of desired characteristics. For instance, in producing wound dressings, additional supports or reinforcement such as mats or linings of woven fibers, or backing layers are required in order to adhere the wound dressing to the skin and to provide other desirable properties to the wound dressing. As an example, a mat or lining of woven fibers may contain materials having antiseptic or wound-healing properties. Surface treatments of the already formed non-woven mats may also provide added benefits in the production of such wound dressings.

It has also been described in PCT Application No. WO 98/03267 to electrostatically spin a wound dressing in place over a wound. In such a use, the body itself is grounded and acts as a collector of the electrospun fibers. This method of synthesizing a wound dressing allows for solution of some of the problems associated with bandage and gauze storage and preparation. It is well known for example, that gauze and bandages must be stored and maintained in a sterile environment in order to offer the greatest protection in healing wounds. If the gauze or bandages are not sterile, these products offer little help in protecting the wound. Electrospinning a wound dressing in place, over a wound, from a sterile liquid, eliminates these problems.

Electrospinning a wound dressing in place over a wound, however, limits the types of solvents that may be used to only those solvents that are compatible with the skin or other tissue to which the dressing is applied. Examples of such solvents include water, alcohols, and acetone. Likewise, because the types of usable solvents are limited, the types of additives, such as, for example, absorbants, bacteriocides, and antibiotics, that may be used in conjunction with the polymer are also limited to those that are soluble in the particular solvent used. Similarly, the types of polymers that may be used are also limited to those that are soluble in a skin- or tissue- compatible solvent. Biocompatible polymer/ solvent combinations include, for example, poly (ethylenimine)/ethanol, poly(vinylpyrrolidone)/ethanol, polyethylene oxide/water, and poly(2-hydroxymethacrylate)/ethanol+acid. While fibers from such a combination are non-reactive in their state as spun, exposure of the fibers to fluids, either from a wound or from external sources, may cause a local pH change from a neutral or nearly neutral pH to one that is acidic or alkaline, depending on the composition of the fiber. For example, when poly(ethylenimine) fiber is exposed to fluid, it will participate in proton transfer, resulting in an alkaline pH in the fluid contacting the polymer. The creation of an undesirable pH environment may cause side effects, such as slow wound healing.

As mentioned above, electrospinning involves the creation of a jet of fluid in an electrical field. The jet of fluid elongates and hardens or drys as it travels toward its target. The resulting fibers are deposited in a random and diffuse manner. This results in material being deposited outside the target area, causing waste. The general electric field on which formation of fibers depends, may also preclude deposition of fibers in the deepest part of a laceration or other deep wound, because fibers will be attracted to and deposit themselves on the portion of the wound closest to the electrospinning apparatus. The rate of hardening or drying is also dependent on factors such as the path length of the jet of fluid. This, in turn, influences the physical characteristics of the non-woven article.

Therefore, the need continues to exist for a wound dressing or other non-woven mat or membrane that is both strong and fluid absorbant. The need also exists for a wound dressing or other non-woven mat or membrane that is electrospun from biocompatible polymers and does not create an undesirable pH environment in the area of the polymer. The dressing or other non-woven mat should, however, still maintain all of the advantages provided in electrospinning the fiber(s) forming the dressing. There is also a need for a method of, and apparatus for, electrospinning a medical dressing or other non-woven mat or membrane that focuses the resulting fibers onto a specified target area. There is also a need for a method of, and apparatus for, the electrospinning of nanofibers which contain additives, without regard to their solubility in a biocompatible solvent/ polymer combination. Likewise, there is also a need for a method of manipulating the rate of hardening of the electrospun fibers, and thereby manipulating the properties of the non- woven mat or membrane which is comprised of the electrospun fibers.

SUMMARY OF INVENTION

It is, therefore, an object of the present invention to provide electrospun fibers which are both strong and fluid absorbent.

It is another object of the present invention to provide an improved medical dressing for the treatment of a wound or other area of a patient requiring protection from contamination, comprising fibers which are both strong and fluid absorbent and optionally contain a pH adjusting component.

It is another object of the present invention to provide an improved medical dressing, as above, wherein the fibers of the dressing are electrospun.

It is still another object of the present invention to provide an improved medical dressing, as above, which may be applied to the wound by electrospinning in a more deliberately focused manner than previously known in the art.

It is still another object of the present invention to provide an improved medical dressing, as above, which can be readily applied to cover wounds having a wide range of sizes and shapes.

It is yet another object of the present invention to provide an improved medical dressing, as above, wherein the fibers forming the dressing are directly applied to a wound.

It is a further object of the present invention to provide an improved method for treating a wound of a patient.

It is still a further object of the present invention to provide a method for treating a wound, as above, wherein the fibers forming the wound dressing are directly applied to the wound.

It is yet a further object of the present invention to provide a method for treating a wound, as above, wherein the dressing is easily removable and is applied in a less painful manner than other traditional wound dressings.

It is still another object of the present invention to provide a single device for electrospinning composite polymer fibers and applying the composite polymer fibers to a wound surface.

At least one or more of the foregoing objects, together with the advantages thereof over the known art relating to electrostatic fiber spinning and wound dressings, which shall become apparent from the specification that follows, are accomplished by the invention as hereinafter described and claimed.

In general, the article of the present invention provides at least one fiber that has been formed by electrospinning a substantially homogeneous mixture of a polymer which is at least weakly hydrophobic, a hydrophilic polymer, and optionally, a pH adjusting component. Generally, at least weakly hydrophobic polymer fibers are fibers with an equilibrium moisture content of less than about 50 percent. Hydrophilic polymer fibers are fibers with an equilibrium moisture content of greater than about 60 percent. Polymer fibers with an equilibrium moisture content of greater than or equal to about 80 percent are generally considered hydrogels.

The article of the present invention also provides a fibrous matrix membrane comprising at least one fiber that has been electrospun as described hereinabove. This aspect of the present invention may take the form of a medical dressing. The article of the present invention may also be applied directly onto the three-dimensional topography of a wound to form the a medical dressing. The at least one fiber of this aspect of the present invention comprises a substantially homogeneous mixture of: a polymer which is at least weakly hydrophobic, a hydrophilic polymer, and optionally, a pH adjusting component. The article of the present invention may also optionally comprise one or more therapeutical performance enhancing compounds, including, for example, antibiotic compounds bacteriocidal compounds, fungicidal compounds, bacteriostatic compounds, crosslinking compounds, analgesic compounds, thrombogenic compounds, nitric oxide releasing compounds such as sydnonimines and NO-complexes that promote wound healing, other pharmaceutical compounds, adhesives, fragrances, odor absorbing compounds, and nucleic acids, without regard to solubility in a biocompatible solvent. In contrast to previous electrospun fibers, the additives are not limited to those that are soluble in the polymer/solvent combination. It has been discovered that even insoluble additives may be added to the polymer/solvent combination of the present invention without separation or segregation of the additive from the polymer in the electrospun fibers. Therefore, the term fluid, when used herein to describe the polymer/solvent combination of the present invention, is to be understood to include suspensions of particles that are insoluble in a given solvent.

Another aspect of the present invention is a method of making at least one fiber comprising electrospinning a substantially homogeneous mixture of: a solvent, a polymer which is at least weakly hydrophobic, a hydrophilic polymer, and optionally, a pH adjusting component.

Another aspect of the present invention is a method of making a fibrous matrix membrane comprising electrospinning a substantially homogeneous mixture of: a solvent, a polymer which is at least weakly hydrophobic, a hydrophilic polymer, and optionally, a pH adjusting component.

Another aspect of the present invention is a method of making a medical dressing whereby fibers are electrospun from a substantially homogeneous mixture comprising: a solvent, a polymer which is at least weakly hydrophobic, a hydrophilic polymer, and optionally, a pH adjusting component, with the resulting fibers being deposited on a suitably charged collection area and removed for subsequent usage.

In another aspect of the invention, the fibers are electrospun as described above and are deposited directly on its intended usage area without first applying the fibers to a transient, charged receiver or subjecting it to other intermediate fabrication steps. When the fibers are applied directly to a wound, the dressing can be made to accommodate any size or shape of wound. According to this aspect of the invention, the fibers are electrospun from a substantially homogeneous mixture of: a solvent, a polymer which is at least weakly hydrophobic, a hydrophilic polymer, and optionally, a pH adjusting component. Further, according to this aspect of the invention, when the fibers are electrospun directly onto a wound surface, the polymeric materials from which the fibers are electrospun are dissolved or suspended in a biocompatible solvent. Also according to this aspect of the invention, the initial polymeric liquid or solution employed may additionally comprise one or more pharmaceutical or therapeutical additives. The additives are not limited to those that are soluble in the biocompatible solvent or polymer/solvent combination. It has been discovered that even insoluble particulate additives may be dispersed in the polymer/solvent combination of the present invention without resulting in separation or segregation of the additive from the polymer in the electrospun fibers.

The method of making a medical dressing of the present invention also provides a method whereby the medical dressing is applied directly onto the three-dimensional topography of the wound to form the a medical dressing. According to this aspect of the present invention, fibers are electrospun from a mixture of: a solvent, a polymer which is at least weakly hydrophobic, a hydrophilic polymer, and optionally, a pH adjusting component. According to this aspect of the present invention, the electrospun fibers are focused onto a target area rather than being widely dispersed as previously known for electrospun fibers.

The present invention further provides a method of using a medical dressing comprising electrospinning one or more fibers to form a fibrous matrix membrane suitable for covering the wound. The fibers of the membrane are either directly assembled to the wound or first applied to a transient, charged receiver and/or subjected to other intermediate fabrication steps. The electrospun fibers in the method of the present invention comprise fibers which are a composite of: a polymer that is at least weakly hydrophobic, a hydrophilic polymer, and optionally a pH adjusting component. According to this aspect of the present invention, the fibers may also optionally comprise one or more therapeutic performance enhancing compounds, including, for example, antibiotic compounds, bacteriocidal compounds, fungicidal compounds, bacteriostatic compounds, crosslinking compounds, analgesic compounds, other pharmaceutical compounds, adhesives, fragrances, odor absorbing compounds, and nucleic acids. These compounds are applied to the treatment area via the wound dressing. The additives that may be applied to a wound via this aspect of the invention are not limited to those that are soluble in the polymer/solvent combination. It has been discovered that even insoluble additives may be added to the polymer/solvent combination of the present invention without separation or segregation of the additive from the polymer in the electrospun fibers. Therefore, the term fluid, when used herein to describe the polymer/solvent combination of the present invention, is to be understood to include suspensions containing particles that are insoluble in a given solvent.

The present invention also provides an apparatus for synthesizing at least one polymer fiber, the apparatus comprising: at least one reservoir, at least one device for electrospinning at least one fiber, the at least one device being in fluid communication with the at least one reservoir; a mixing device for agitating the fluid within the reservoir; and a power source capable of generating an electric field in electrical communication with the at least one device.

In another aspect of the present invention, the apparatus comprises a housing containing at least one reservoir for containing a fluid, a device for electrospinning the fluid into at least one fiber, the device being in fluid communication with the reservoir; a power source capable of generating an electric field in electrical communication with the device; and an extension extending from the housing for spacing the electrospinning device from the injured area, and a means for focusing the electrospun fibers into a defined area; wherein the fibers comprise: a polymer that is at least weakly hydrophobic, a hydrophilic polymer, and optionally a pH adjusting component.

The present invention also provides an apparatus for directly applying and assembling a plurality of electrospun fibers to a three dimensional surface of a wound either with or without any intermediate fabrication steps such as use of a transient, charged receiver, the apparatus comprising: at least one device for electrospinning at least one fiber; at least one reservoir for containing a fluid from which the at least one fiber is electrospun, the reservoir being in fluid communication with the at least one device for electrospinning the at least one fiber; a mixing device for agitating the spinning material; a power source in electrical communication with the at least one device for electrostatically spinning the at least one fiber; and a means for focusing the electrospun fibers into a defined area.

In one aspect of the present invention, the apparatus may further include a housing for encasing the other recited components of the apparatus and one or more legs or extensions connected to the housing for supporting the apparatus and/or for maintaining optimal spacing from the surface of the wound during use. The apparatus may use the patient's body to attract the electrically charged fibers and, therefore, it is noted that the grounded electrical terminal of the apparatus may be connected to the patient by a separate wire or the like in a manner known in the art in order to aid in attracting or assembling the plurality of fibers onto the wound surface.

PREFERRED EMBODIMENT FOR CARRYING OUT THE INVENTION

In general, the article of the present invention is at least one electrospun fiber comprising a polymer that is at least weakly hydrophobic and a hydrophilic polymer. Polymeric materials suitable for electrospinning into fibers may include, for example, those inert polymeric substances that are absorbable and/or biodegradable, that react well with selected organic or aqueous solvents, or that dry quickly. Essentially any organic or aqueous soluble polymer or any dispersions of such polymer with a soluble or insoluble additive suitable for topical therapeutic treatment of a wound may be employed. Examples of such suitable polymers include, but are not limited to, linear poly (ethylenimine), cellulose acetate, and other preferably grafted cellulosics, poly (L-lactic acid), poly(caprolactone), poly (ethyleneoxide), and poly vinylpyrrolidone.

In one embodiment, the article of the present invention is at least one electrospun fiber, as above, additionally comprising a pH adjusting component.

In another embodiment, the article of the present invention comprises a fibrous non-woven matrix of electrospun fibers comprising a polymer that is at least weakly hydrophobic, a hydrophilic polymer and optionally, a pH adjusting component.

In another embodiment, the article of the present invention comprises a medical wound dressing for protecting wounds. In this embodiment, the article of the present invention comprises: a polymer that is at least weakly hydrophobic, a hydrophilic polymer, optionally, a pH adjusting component, and also optionally, at least one pharmaceutical or therapeutical agent. The medically tailored membranes which form the wound dressings of this embodiment may be formed as the electrospun fibers are deposited painlessly and directly onto the wound in any desired size, thickness or shape. Because most wounds are three dimensional in character, it will be appreciated that the membrane of the present invention can be constructed and assembled directly in accordance with the three dimensional topography of the wound, thereby providing better protection to the wound and enabling more direct and complete delivery of any medically important additives which are incorporated in the dressing, to the wound. This embodiment of the present invention is focused into a defined area, thereby allowing greater penetration of the fibers into deep wounds such as lacerations, and therefore, improved protection of the wound and delivery of pharmaceutical or therapeutical agents. Membranes, usually in the form of films that conform to the wound in this way, are sometimes called "spray on" wound dressings.

It will be appreciated that the medically tailored, polymeric fibrous membrane of the above embodiment is relatively inexpensive to make due to the ability of the electrospun fibers to be applied directly onto the affected wound area to the desired size and surface characteristic of the wound in a focused manner. The freshly formed membrane is also inherently sterile.

In another embodiment of the present invention, the article of the present invention comprises a medical dressing as above, that is produced by electrospinning a fluid into at least one fiber which is collected on a receiving area and removed for later application to the wound surface, the fluid comprising: a polymer that is at least weakly hydrophobic, a hydrophilic polymer, optionally, a pH adjusting component, and also optionally, at least one pharmaceutical or therapeutical agent. The medical dressing of this embodiment may not only protect or repair the wound, but optionally, may also deliver topical analgesics or other like pharmaceutical or therapeutical agents to the wounded tissue of the patient.

As discussed earlier, one of the major advantages of using electrostatically spun fibers in wound dressings, is that these fibers can be produced having very small diameters, usually on the order of about 3 nanometers to about 3000 nanometers, and more preferably, on the order of about 10 nanometers to about 500 nanometers, and most preferably, on the order of about 10 nanometers to about 100 nanometers. Thus, given that these "nanofibers" can be formed into non-woven membranes of any desired shape and thickness relatively rapidly, their usefulness and desirability in medical dressings can readily be appreciated.

Because of the very small diameter of the fibers, a membrane with very small interstices and high surface area is produced. In turn, the resultant medical dressing is microporous and breathable, but is resistant to high air flow. These are important and desirable characteristics of medical dressings. Generally, pores sizes for the medical dressing produced using electrospinning techniques range from about 500 nanometers to about 1 micron, small enough to protect the wound from bacterial penetration via aerosol particle capture mechanisms. Pore sizes in this range may also hinder the passage of viral particles through the dressing to the wound. The electrospun polymer matrix membranes of the present invention have high surface areas of at least 5 $m^2/g$, and more preferably, approximately 100 $m^2/g$ for efficient fluid absorption and dermal delivery. The high surface areas also impart high hemostatic potential for the dressing.

The electrospun fiber-formed membranes and the resultant medical dressings of the present invention are lightweight, oxygen and moisture permeable, yet are wind resistant for protection against airborne contaminants such as dust, microbes, or other infectious agents which might be carried by the air currents. The ability of the membrane fibers to transport and deliver therapeutic additives to the site of the wound is also important. This ability to transport and deliver additives can be controlled through the choice of polymer carrier, density and thickness of the applied membrane, and/or layering of different membrane fiber compositions.

With respect to the fibers, it will be understood that the fibers should preferably be dry so as to have sufficient strength in forming the membrane. However, in some instances, a wet fiber may be employed. Such wet fibers are generally softer and conform to the surface of the skin better. Other advantages may include those set forth previously in discussion of U.S. Pat. No. 4,043,331. In any event, the ability to electrospin the fibers of the present invention directly onto the surface of the wound allows for improved -flexibility in the composition of the fibers, improved porosity of the membrane, and improved strength, all in a less expensive and more timely manner. Moreover, the direct application of the fibers means that the fibers can be advantageously placed in intimate contact with the total wound surface. This enables efficient removal of dead cells, fluid or bacteria from deep within the wound when the dressing is changed, thereby reducing or eliminating the need for debridement of the wound. Direct contact with the surface of the wound will also enable improved drug delivery to the wound. Finally, it will be appreciated that direct application provides for improved and, in fact, inherent, sterility of the fibers and, therefore, the dressing, thereby eliminating the need for gamma radiation or other treatments to disinfect the dressing materials. In addition, controlled generation of ozone and other active species may be used to assist with sterilization.

In one embodiment, the polymer is in the form of a closed cell foam to protect the treated area against mechanical disturbance or to provide thermal insulation.

Electrospinning is well known in the fiber forming arts and generally involves the introduction of a liquid (e.g., a solution or dispersion) into an electric field, so that liquid jets having an electrical charge are formed and elongated from the surface of the liquid. These electrically charged jets (to be fibers) are generally drawn to a collector at an attractive electrical potential. The collector, in this case, may be the body of the patient. During the formation of the liquid jets into fibers, they become much longer and thinner and generally cool, harden, and/or dry enough to be strong prior to contacting the surface of the wound. They then quickly form a protective sheath or membrane on the wound.

The results of the present invention have been enabled by the development of electrospinning techniques which allows for the processing of soluble polymers from both organic and aqueous solvents. Furthermore, it has been discovered that dispersions of discrete particles and soluble non-fiber forming additives into the fluid to be spun into the fiber (i.e., the spin dope) does not prevent the formation of membranes using electrospinning techniques. Such additives may, therefore, be incorporated into the fibers and membranes for useful purposes.

The polymer membrane forming the medical dressing of the present invention is generally formulated from a plurality of fibers electrospun from a substantially homogeneous mixture of any of a variety of hydrophilic and at least weakly hydrophobic polymers, that can be optionally blended with any of a number of medically important wound treatments, including analgesics and other pharmaceutical or therapeutical additives. Such polymeric materials suitable for electrospinning into fibers may include, for example, those inert polymeric substances that are absorbable and/or biodegradable, that react well with selected organic or aqueous solvents, or that dry quickly. Essentially any organic or aqueous soluble polymer or any dispersions of such polymer with a soluble or insoluble additive suitable for topical therapeutic treatment of a wound may be employed. Polymer solutions may optionally be applied in a sterile condition. Examples of suitable hydrophilic polymers include, but are not limited to, linear poly(ethylenimine), cellulose acetate and other grafted cellulosics, poly (hydroxyethylmethacrylate), poly (ethyleneoxide), and poly vinylpyrrolidone. Examples of suitable polymers that are at least weakly hydrophobic include acrylics and polyester such as, poly(caprolactone), poly (L-lactic acid), poly (glycolic acid), similar co-polymers of theses acids.

As suggested hereinabove, other additives, either soluble or insoluble, may also be included in the liquid(s) to the electrospun into the fibers. Preferably, these additives are medically important topical additives provided in at least therapeutic effective amounts for the treatment of the patient. Such amounts depend greatly on the type of additive and the physical characteristics of the wound as well as the patient. Generally, however, such additives can be incorporated in the fibers in amounts ranging from trace amounts (less than 0.1 parts by weight per 100 parts polymer) to 500 parts by weight per 100 parts polymer, or more. Examples of such therapeutic additives include, but are not limited to, antimicrobial additives such as silver-containing antimicrobial agents and antimicrobial polypeptides, analgesics such as lidocaine, soluble or insoluble antibiotics such as neomycin, thrombogenic compounds, nitric oxide releasing compounds such as sydnonimines and NO-complexes that promote wound healing, other antibiotic compounds, bacteriocidal compounds, fungicidal compounds, bacteriostatic compounds, analgesic compounds, other pharmaceutical compounds, adhesives, fragrances, odor absorbing compounds, and nucleic acids, including deoxyribonucleic acid, ribonucleic acid, and nucleotide analogs.

In still another embodiment, additives that contribute to the structural properties of the article may be added. These include small solid particles, dispersed droplets of immiscible liquids in which other substances may be dissolved, crosslinking compounds, blowing agents to create foams, adhesives, elastomers and the like, which may be chosen for their function in protecting and healing the wound.

It will be appreciated that the fibers can produce a number of different types of membranes depending upon how the fibers are produced and deposited. In one embodiment, the liquid to be electrospun into the plurality of fibers is a mixture of: a polymer that is at least weakly hydrophobic, a hydrophilic polymer, optionally, a pH adjusting component, and also optionally, at least one pharmaceutical or therapeutical agent. Thus, one fluid could provide the entire membrane. However, it is also envisioned that fibers of additional different compositions could be spun together or in sequential layers to provide a suitable membrane.

In general, the method of using the medical dressing of the present invention comprises applying fibers to a wound or other area needing protection from contamination or area requiring treatment with therapeutical or pharmaceutical compounds, to form a fibrous non-woven matrix, wherein the fibers are electrospun from a substantially homogeneous mixture comprising a hydrophilic polymer and a polymer which is at least weakly hydrophobic.

In one embodiment, the method of using the medical dressing of the present invention comprises applying fibers, as above, that are electrospun from a substantially homogeneous mixture comprising a hydrophilic polymer, a polymer which is at least weakly hydrophobic, and a pH adjusting compound.

In another embodiment, the method of using the medical dressing of the present invention comprises applying fibers, as above, that are electrospun from a substantially homogeneous mixture comprising a hydrophilic polymer, a polymer which is at least weakly hydrophobic, a pH adjusting compound, and at least one pharmaceutical or therapeutical agent.

In another embodiment, the at least one pharmaceutical or therapeutical agent is selected from the group consisting of antibiotic compounds such as bacteriocidal and fungicidal compounds, bacteriostatic compounds, crosslinking compounds, analgesic compounds, thrombogenic compounds, nitric oxide releasing compounds such as sydnonimines and NO-complexes that promote wound healing, other pharmaceutical compounds, adhesives, fragrances, odor absorbing compounds, and nucleic acids, without regard to solubility in a biocompatible solvent. In contrast to previous electrospun fibers, the additives are not limited to those that are soluble in the polymer/solvent combination. It has been discovered that even insoluble additives may be added to the polymer/solvent combination of the present invention without separation or segregation of the additive from the polymer.

In another embodiment, the method of using the medical dressing of the present invention comprises applying fibers, as above, that are electrospun from a substantially homogeneous mixture comprising a hydrophilic polymer, and a polymer which is at least weakly hydrophobic, wherein the medical dressing is applied directly onto the three-dimensional topography of the wound to form the medical dressing.

In another embodiment of this invention, the electrospun fibers described above are deposited in a focused manner onto a target area.

In general, the apparatus of the present invention comprises: at least one device for electrospinning at least one fiber; at least one reservoir for containing a fluid from which at least one fiber is electrospun, the reservoir being in fluid communication with the at least one device for electrospinning the at least one fiber; a means for mixing the fluid within the reservoir; a power source in electrical communication with the at least one device for electrostatically spinning the at least one fiber; and a means for focusing the electrospun fibers into a defined area.

In one embodiment, the apparatus is small enough to be portable or even handheld, thereby allowing for its immediate use on the patient at the on-site location of the wounded patient prior to transport.

In another embodiment, the apparatus may further include a housing for encasing the other recited components of the apparatus and one or more legs or extensions connected to the housing for supporting the apparatus and/or for maintaining optimal spacing from the surface of the wound during use.

In another embodiment, the apparatus may use the patient's body to attract the electrically charged fibers. In such an embodiment, the power source is in electrical communication with a grounded electrical terminal of the apparatus which is connected to the patient by a separate wire or the like in a manner known in the art in order to aid in attracting or assembling the plurality of fibers onto the wound surface.

In another embodiment, the means for focusing the electrospun fibers into a defined area comprises a directed stream of gas which directs the fibers away from the device for electrospinning and toward the target. Such an embodiment may comprise a gas delivery system which directs one or more annular streams of gas toward the target area, thereby containing and directing the fibers to the target area.

In another embodiment, the means for focusing the electrospun fibers may comprise one or more focusing electrodes. In one such embodiment it is envisioned that the electrodes may be in the form of one or more ring shaped electrodes located between the device for electrospinning and the target. By giving these electrodes a predetermined electric potential, the course of the fibers may be altered. For example, by giving a ring shaped electrode the same electrical charge as fibers, the fibers will be directed toward the interior of the electrode, thereby focusing the fibers to a relatively constrained area. It is also envisioned that it may be desirable in some applications to alter the distribution of the fibers to include a wider area than would be otherwise possible. In such a case the ring type electrode would be given the opposite charge of the fibers thereby distributing them to a wider area than would be otherwise possible. It is also envisioned that the shapes and sizes of the focusing electrodes may vary according to the characteristics of the intended target.

In still another embodiment, the means for focusing the electrospun fibers may comprise a means for changing the polarity of the electrospinning apparatus and the target. In the course of applying electrospun fibers to a target, a localized charge may exist where fibers have accumulated. Such a localized charge would match the charge of the fibers and would therefore be expected to actually repulse new fibers and prevent their deposition on the intended target. By alternating the charge of the electrospinning device and the target, layers of fibers having an alternating charge may accumulate with less dispersion than would otherwise occur and therefore, a thicker membrane may be produced.

Figure 1:
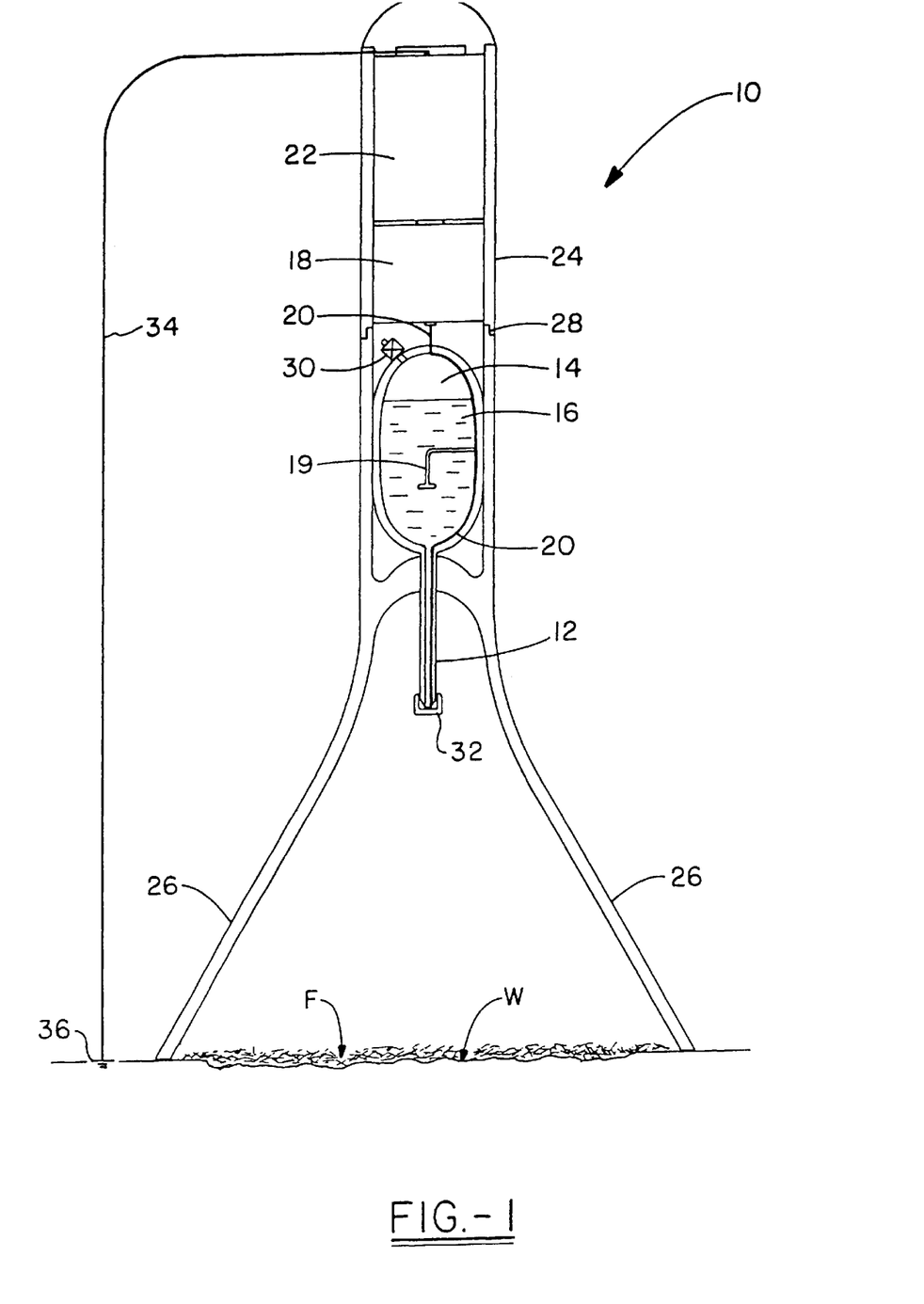
FIG. 1 is a schematic cross-sectional view of a portable apparatus for electrospinning fibers and directly assembling the fibers to the wound treatment area of a patient in accordance with the concepts of the present invention.

It will further be appreciated that the "spray on" medical dressings may be produced using a portable apparatus such as the one schematically represented in FIG. 1 by the numeral 10. The portable electrospinning apparatus 10 may be used not only to produce the electrospun fibers to be employed in the medical dressing of the present invention, but also to directly apply and assemble the plurality of electrostatically spun fibers, denoted generally in FIG. 1 by the letter F, to a three dimensional surface of a wound, denoted generally in FIG. 1 by the letter W, without the use of a transient, charged receiver, or other temporary, immediate of any kind, which could then take the form of a bandage.

The portable apparatus 10 includes at least one device 12 for electrostatically spinning the plurality of fibers. Such device 12 is well known in the art and operates in a manner well known to those skilled in the art. At least one reservoir 14 containing a fluid such as 16, from which one or more fibers (F) are electrostatically spun, is located preferably proximate to the electrospinning device 12 and is in fluid communication therewith. A power source 18 may be housed in the apparatus 10 and is in electrical communication with the electrospinning device 12 such as by a wire 20 extending into and around the reservoir 14 and leading to the device. A battery pack 22 may also be installed in the apparatus 20 and operatively connected to the power supply 18 to provide renewable energy thereto. Essentially any battery capable of meeting the needs of the device can be used, including known 1.5 volt alkaline batteries, high energy lithium batteries, 12 volt lead acid batteries, rechargeable batteries, etc. In one embodiment a mixing device 19 for agitating fluid 16 is located within reservoir 14.

In another embodiment, mixing device 19 is a sonication device. In yet another embodiment, mixing device 19 is a sonication device attached to the side of reservoir 14, which mixes fluid 16 by sending sound waves through the walls of reservoir 14.

In still another embodiment, mixing device 19 is located within reservoir 14, but is freely movable within reservoir 14 and assists in mixing fluid 16 by physical agitation such as, for example, during physical shaking of reservoir 14 or apparatus 10. The mixing device of such an embodiment may be likened to a ball inside a can of spray paint which mixes the spray paint when the can is shaken.

Each of the above-mentioned components of the apparatus 10 may be encased within a housing 24 for the device. Extending from the housing 24 are one or more pairs of legs 26 for supporting the apparatus 10 and/or for maintaining optimal spacing of the device 12 from the surface of the wound (W) during use. This will provide the fibers with sufficient time to dry before contacting the skin surface. It will be appreciated that the legs 26 may, in an alternative embodiment be a single extension completely surrounding the wound area to be treated. There may also be some sort of insulating shield extending from the housing 24 to prevent the tip of the device 12 from being touched.

Preferably, the apparatus 10 will be small enough to be handheld, thereby allowing for its immediate use on the patient at the on-site location of the wounded patient prior to transport. This would be particularly useful on battlefields or in situations where the patient could not be readily transported, such as in automobile accidents where the patient is entrapped in the vehicle.

In operation, the apparatus 10 first is filled with a desired liquid or fluid capable of being electrospun into a fiber. It is envisioned that the housing 24 of the apparatus 10 could be separated in some manner as at 28 to gain access to the liquid reservoir 14. Of course, the liquid reservoir 14 could also be filled at its place of manufacture for one-time use. Access into the reservoir 14 can be gained through inlet valve 30. Nonsoluble additives may be kept in homogeneous suspension by engaging mixing device 19.

Once the reservoir is filled and the battery charged, the apparatus 10 is used by breaking off or otherwise removing the tip or cap such as 32 near the electrospinning device 12. The electrical potential that causes the electrospinning process to occur is applied to the liquid 16 and to the device 12 near the tip 32 which are in electrical contact.

The breaking of the tip exposes the liquid or fluid and the electrical forces eject a jet of the liquid out of the device 12 which solidifies to form nanofibers or one very long nanofiber. It will be appreciated that, in this case, the fibers are attracted to the wound which is maintained at ground potential by a wire such as 34 or other electrical conductor connected to a ground terminal 36, which may be the ground terminal of the apparatus 10 as well, as is well known in the art. That is, the apparatus 10 and the body of the patient are electrically grounded, and such ground terminal may be employed by both the apparatus 10 and the patient. Alternatively, the patient may be grounded simply by holding the hand of the operator of the apparatus 10, the ground terminal being the same for both the apparatus and the patient.

Figure 2:
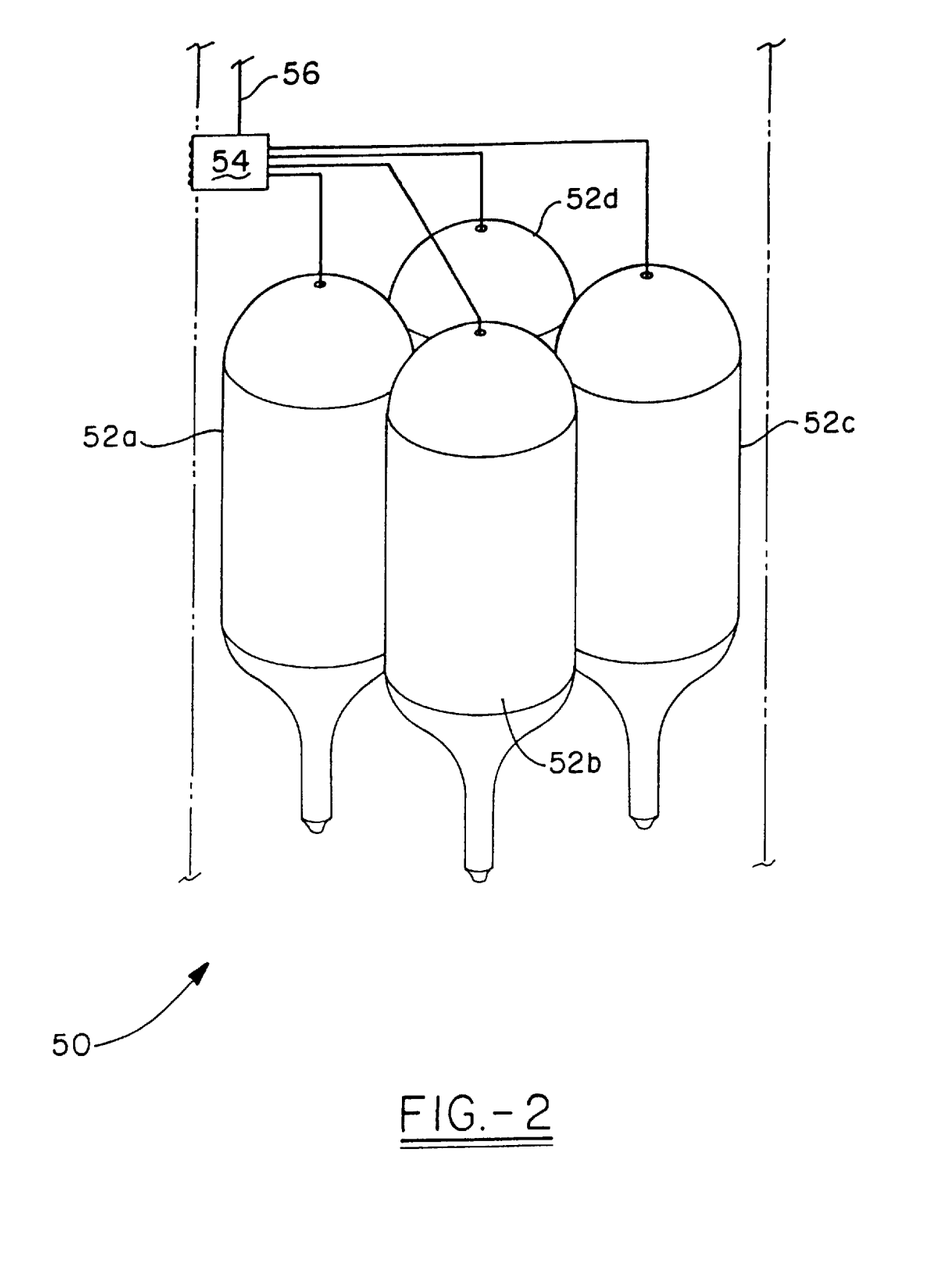
FIG. 2 is a schematic perspective view of a portion of a portable device with multiple reservoirs for use in the production of fibers that may be directly applied to the surface of a wound of a patient in accordance with the concepts of the present invention.

FIG. 2 shown a schematic representation of a section, generally denoted as 50, of the apparatus of the present invention, and in particular, the section containing the liquid reservoir. In FIG. 2, multiple liquid reservoirs 52a, 52b, 52c and 52d are contained within the housing (shown in phantom) such that they may be used simultaneously or independently of each other. Each reservoir 52 can contain a polymer or polymer solution different from the others. This allows for the easy application of several types of nanofibers, either simultaneously or sequentially.

In one embodiment, reservoir 52a may be filled with a solution providing for excellent absorbency; reservoir 52b may be filled with a solution containing an antibiotic; reservoir 52c may be filled with a solution to be used as an internal dressing layer; and reservoir 52d may be filled with a solution to be used as an external protective layer. In will be appreciated that any one of these reservoirs can be used to appropriately layer the fibers for the dressing or can be used simultaneously.

In the embodiment shown, a selector switch 54 is shown which provides for the electrospinning of the liquid. The switch 54 is connected to the power supply (not shown) such as by wire 56 and can be developed as is well known in the art to operate any, some or all of the liquid reservoirs.

With respect to layering of different membrane fiber compositions, it will be appreciated that many of the desired functions of the dressing can be built into the dressing 30 by layering specific features during electrospinning of the fibers. For example, certain layers may include releasing agents or complexes which release medically important additives into the wound. For instance, fibers containing high concentrations of antibiotic and/or tissue repairing drugs could be located proximate the surface of the wound, while antimicrobial compounds could be concentrated near or in the exterior layers of the dressing. In an alternative embodiment, interior dressing layers may include fibers providing high absorbency, while exterior layers may include fibers for water repellancy.

It will be appreciated that essentially any organic or aqueous solvent suitable for dissolving the desired polymer and capable of being electrospun can be employed. Solvents that would irritate or trouble the wound could be used if they suitably evaporated before the fiber reached the wound. Non-limiting examples of such suitable solvents include acetone, tetrahydrofuran, ethanol or other low molecular weight alcohols, and water. It will further be appreciated that the therapeutic additives may be solvent or insoluble in the solvent. Where the additives are insoluble, they may be encapsulated within the fibers using the electrospinning techniques described. It has been found that fibers produced from these electrospinning techniques with such additives still impart the desired properties of the additive and yet maintain the porous membrane-like properties of the nanofibrous dressing as described.

The following examples should not be viewed as limiting the scope of the invention. The claims will serve to define the inventions.

GENERAL EXPERIMENTATION

Example 1

Wound dressings utilizing fibers containing Polycaprolactone and/or Linear Polyethylenimine Materials:

Polycaprolactone (PCL) with an average molecular weight of 120,000 was purchased from Scientific Polymer Products, Inc. and was used as is. Linear Polyethylenimine (LPEI) was synthesized from 500,000 average MW Polyethyloxazoline. The latter was purchased from Sigma Chemical Co. The pH adjusting compound carboxypolymethylene, sold under the tradename Carbopol® (974P NF, Lot No: AB07525), was purchased from B.F. Goodrich while Alginic acid was obtained from Sigma Chemical Co.

Method: Polycaprolactone was dissolved in acetone to make an 18% (w:w) solution. Linear polyethylenimine was dissolved in ethanol making a 25% (w:w) solution. From these solutions, various samples were mixed. The ratio of 20:80 LPEI:PCL (w:w) was used for spinning the LPEI:PCL mixture. Moreover, several pH adjusting components were used with the spinning mixtures. When alginic acid or Carbopolg were used, the percentage was 2.9% of the total weight of both polymers (PCL & LPEI). In order to mix the components for spinning, alginic acid first was suspended in a small amount of ethanol. Then LPEI solution was added and finally PCL solution was mixed with them and the final mixture was spun immediately to avoid any pH adjusting component aggregation. In the case of Carbopol®, first it was suspended in a small amount of acetone then PCL solution was added and finally LPEI solution was mixed together with them and the final mixture was also spun right away to avoid any pH adjusting component aggregation.

To measure the degree of absorbency, a 1.5 cm² piece of the fiber matt was cut and weighed (dry weight or DW). The fiber was then was soaked in either water or saline (pH: 7) solution for different period of times. The liquid was drained and the fiber was dried and weighed (wet weight or WW)

Equations:

1. Liquid uptake:

$$\frac{WW - DW}{DW} \times 100$$

2. Equilibrium Liquid Content:

$$\frac{WW - DW}{WW} \times 100$$

It is to be understood that the terms equilibrium liquid content, equilibrium water content and equilibrium buffer content are equivalent in meaning and reference should be made to the above formula with respect to each of these terms.

pH values of the liquids were determined after soaking the fiber in them for 24 hours. The fiber matt does not dissolve in water and the fiber is still strong even after soaking for more than 10 days.

Sample 1:
Spinning PCL alone. A solution of 18% (w:w) PCL in acetone was made and spun with 23 KV at 7 inch (17.8 cm) gap distance at room temperature. It gave very strong white fibers with variable size around 1 µm.

Sample 2:
Spinning PCL with Carbopol® as a pH adjusting component. A solution of 18% (w: w) PCL in acetone was made and 2.9% (w: w) Carbopol® was mixed with it. The mixture was spun with 24 KV at 7.5-inch (19.1 cm) gap distance at room temperature. The fiber was white and very strong with variable size around 1 µm.

Sample 3:
Spinning PCL with alginic acid as a pH adjusting component. A solution of 18% (w: w) PCL in acetone was made and 2.9% (w: w) alginic acid was mixed with it. The mixture was spun with 15 KV at 6.5-inch (16.5 cm) gap distance at room temperature. The fiber was white and very strong with variable sized around 1 µm.

Sample 4:
Spinning LPEI alone. A solution of 25% (w: w) LPEI in ethanol was made and spun with 23 KV at 7 inch (17.8 cm) gap distance at room temperature. The fiber was less than 1 µm in size, white and strong.

Sample 5:
Spinning LPEI with Carbopol® as a pH adjusting component. A solution of 25% (w: w) LPEI in ethanol was made and 2.9% (w: w) Carbopol® was mixed with it. The mixture was spun with 19 KV at 6 inch (15.2 cm) gap distance at room temperature. The fiber was less than 1 µm in size, white and strong.

Sample 6:
Spinning LPEI with alginic acid as a pH adjusting component. A solution of 25% (w: w) LPEI in ethanol was made and 2.9% (w: w) alginic acid was mixed with it. The mixture was spun with 15 KV at 7 inch (17.8 cm) gap distance at room temperature. The fiber was less than 1 µm in size, white and strong.

Example 7:
Spinning LPEI and PCL without a pH adjusting component. A solution of 25% (w: w) LPEI in ethanol was made and mixed with a solution of 18% (w: w) PCL in acetone at ratio of 20:80. The mixture was spun with 15 KV at 7 inch (17.8 cm) gap distance at room temperature. The fiber was less than or equal to 1 µm in size, white and very strong.

Sample 8:
Spinning LPEI and PCL with Carbopol® as an pH adjusting component. A solution of 25% (w: w) LPEI in ethanol was made and mixed with a solution of 18% (w: w) PCL in acetone at ratio of 20:80. The 2.9% (w: w) Carbopol® was added. The mixture was spun with 15 KV at 5-inch (12.7 cm) gap distance at room temperature. The fiber was less than or equal to 1 µm in size, white and very strong.

Sample 9:

Spinning LPEI and PCL with alginic acid as a pH adjusting component. A solution of 25% (w: w) LPEI in ethanol was made and mixed with a solution of 18% (w: w) PCL in acetone at ratio of 20:80. The 2.9% (w: w) alginic acid was added. The mixture was spun with 23 KV at 7.5-inch (19.1 cm) gap distance at room temperature. The fiber was less than or equal to 1 $\mu$m in size, white and very strong.

Samples 1–9 were spun into mats of fibers and the mats were tested for their effect on pH and their water absorbency. These comparisons are summarized in Tables 1 and 2 and FIGS. 3 and 4. It will be noted that the equilibrium water content and liquid uptake percentages of mats of fibers will differ from the equilibrium water content of individual fibers because of the surface tension present between fibers in the mat will cause greater water retention than is possible with individual fibers.

TABLE 1 pH Values

|  | PCL | PCL/Carbopol | PCL/Alginate | LPEI | LPEI/Carbopol | LPEI/Alginate | PCL/LPEI/Carbopol | PCL/LPEI/Alginate |
|---|---|---|---|---|---|---|---|---|
| WATER | 6.86 | 6.75 | 6.24 | 8.39 | 8.51 | 6.9 | 7.9 | 7.73 |
| SALINE | 6.84 | 6.85 | 6.77 | 8.29 | 8.42 | 7.56 | 7.75 | 7.58 |

Table 1 shows the pH values of water and saline after soaking samples in them for 24 hours. The data indicate that the addition of a pH adjusting component to the homogeneous mixture of polymers of the present invention brings the pH of liquid that has contacted the fibers closer to neutral than liquid that has contacted homopolymer fibers of hydrophilic LPEI alone.

Table 2 shows the equilibrium moisture content of different fibers after 24 hours. The data demonstrate that PCL/LPEI/Alginate fibers and PCL/LPEI/Carbopol fibers possess similar equilibrium buffer content to LPEI fibers, LPEI/alginate fibers and LPEI/Carbopol fibers.

TABLE 2

Equilibrium Moisture Content of Electrospun Fibers

| Fiber Composition | Equilibrium Moisture Content (percent) |
|---|---|
| LPEI | 92.75 |
| LPEI + Carbopol | 94.69 |
| LPEI + Alginate | 94.48 |
| PCL | 71.31 |
| PCL + Carbopol | 81.91 |
| PCL + Alginate | 91.68 |
| PCL + LPEI + Carbopol | 95.00 |
| PCL + LPEI + Alginate | 93.89 |

Figure 3:
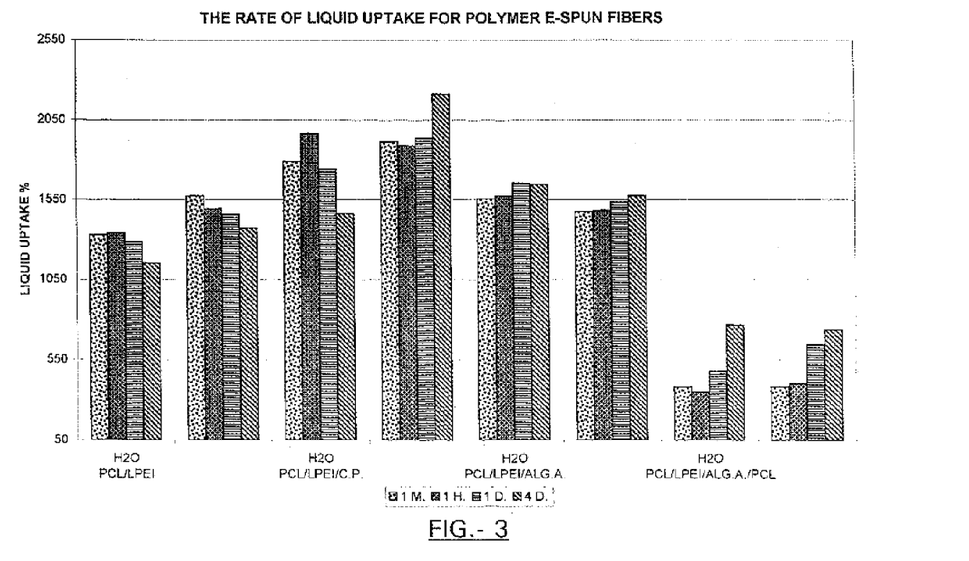
FIG. 3 is chart showing the rate of liquid uptake for mats of electrospun fibers of composite polymers compared to the rate of water uptake for a mat of electrospun fibers that contains layers of hydrophobic polymers, a layer of hydrophilic polymer, and a layer of pH adjusting compound.
Figure 4:
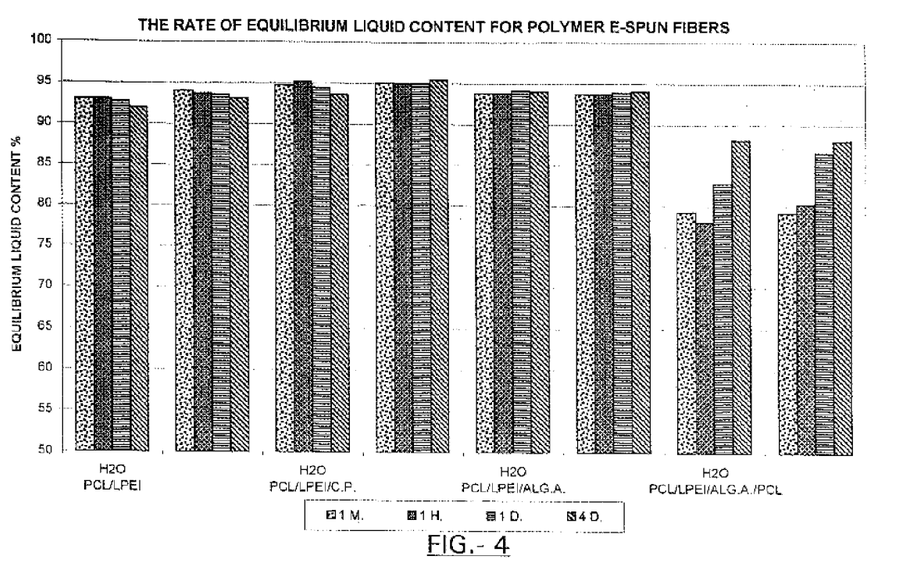
FIG. 4 is chart showing the rate of equilibrium liquid content for mats of electrospun fibers of composite polymers compared to the rate of equilibrium liquid content for a mat of electrospun fibers that contains layers of hydrophobic polymers, a layer of hydrophilic polymer, and a layer of pH adjusting compound.
Figure 5:
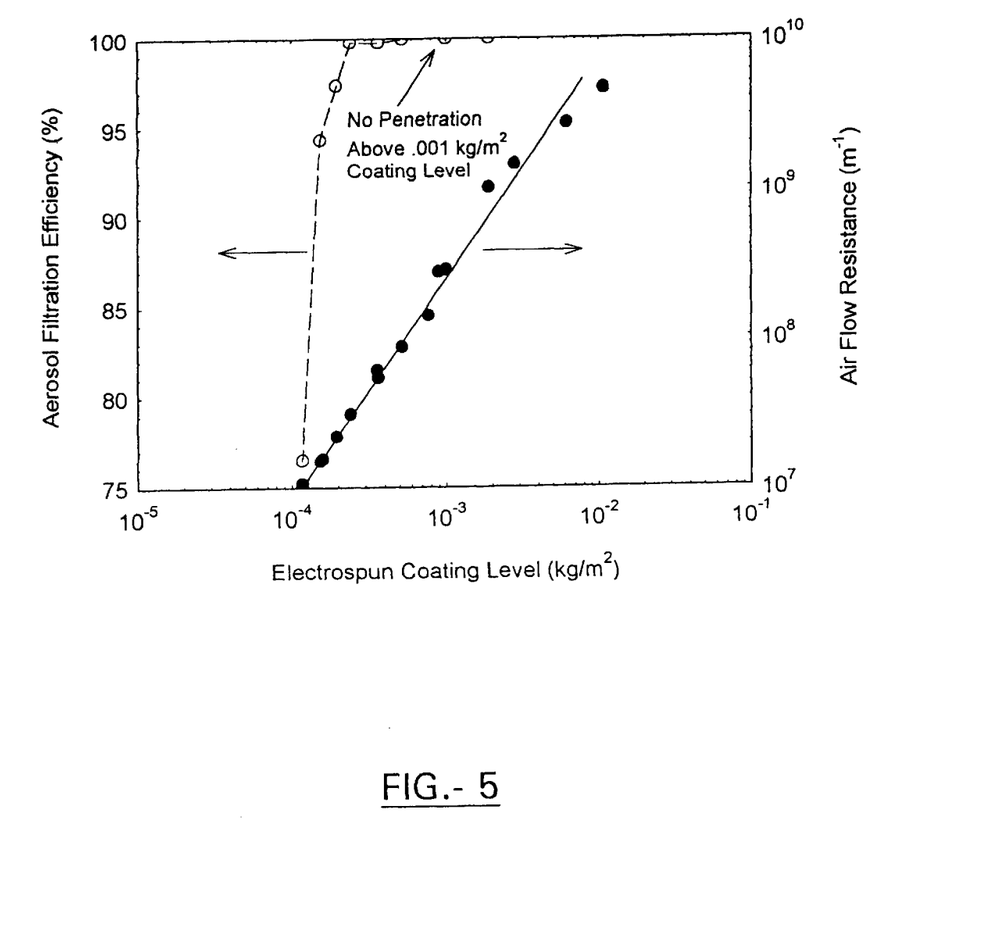

FIGS. 3 and 4 illustrate the uptake of both water and phosphate buffered saline (PBS) over 1 minute (1 M), 1 hour (1 H), 1 day (1 D), and 4 days (4D) for mats of electrospun fibers of composite polymers (PCL/LPEI, PCL/LPEI/C.P., PCL/LPEI/ALG.A.) compared to the rate of water uptake for a mat of electrospun fibers that contains layers of hydrophobic homopolymer fibers, a layer of hydrophilic homopolymer fibers, and a layer of pH adjusting compound (PCL/LPEI/ALG.A./PCL). FIG. 3 shows that PCL/LPEI/alginate fibers and PCL/LPEI/Carbopol fibers exhibit liquid uptake percentages that surpass those of PCL/LPEI/Alginate/PCL layered fiber mats. Similarly, FIG. 4 shows that the equilibrium water content of PCL/LPEI/alginate fibers and PCL/LPEI/Carbopol fibers surpass those of PCL/LPEI/Alginate/PCL layered fiber mats.

Example 2

Production of fibers of various composite polymer solutions.

Materials:

Polycaprolactone (PCL) with an average molecular weight of 120,000 was purchased from Scientific Polymer Products, Inc. and was used as is. Linear polyethylenimine (LPEI) was synthesized from polyethyloxazoline with an average molecular weight of 500,000. The latter was purchased from Sigma Chemical Co. The pH adjusting compound carboxypolymethylene, sold under the tradename Carbopol(& (974P NF, Lot No: AB07525), was purchased from B.F. Goodrich while Alginic acid was obtained from Sigma.

Solutions of Polycaprolactone (PCL), Poly (2-hydroxymethacrylate) (Poly HEMA), Poly (vinyl pyrrolidone)(PVP), Poly (ethyloxazoline)(PEOz), Polyethylene oxide (PEO), and Linear Polyethylenimine (L-PEI) were used to make various composite polymer fibers as described below. PCL and PEO were obtained from Scientific Polymer Products of Ontario, N.Y. Poly HEMA, PVP, and PEOz, were obtained from Polysciences Inc. of Warring, Pa. Various therapeutical additives were also added to several of the spin solutions and were thereby incorporated into the fibers, as described below. Dextran, lidocaine, erythromycin, charcoal, Pluronic F-127, chitosan, and polyethylenimine cellulose were purchased from Sigma Chemical Co. Acetone, methyl salicylate, and isoamyl acetate were obtained from Aldrich Chemical Co., Inc. of Milwaukee, Wis. Rhoplex adhesive was obtained from Rohm and Haas of Philadelphia, Pa.

Sample 10. PCL (12.29 g) was placed into a beaker along with 50 g of acetone. The beaker was heated until the polymer dissolved. Once the polymer was dissolved the solution was stirred and allowed to cool to room temperature. Acetone was then added to the sample to give a 16% solution of PCL in acetone. Depending on the substance(s) added this or a more concentrated solution was used to make the spin-blends. Methyl salicylate, or isoamyl acetate was added to the final solution to increase point of the solution.

Samples 11, 12, and 13. PEOz, PEO, and PVP solutions were all made following the same procedure. Polymer (9.10 g) was placed in a lidded container. To the polymer 47.77 g of the desired solvent were added. Depending on the substance(s) added this or a more concentrated solution was used to make the spin-blends.

Sample 14. L-PEI was synthesized using the Warakomski procedure. Briefly, polyethyloxazoline is dissolved in concentrated sulfuric acid and heated to 80° C. for 24 hours. The solution was neutralized with base and the resulting linear polyethylenimine polymer was recrystalized from hot water. Once synthesized, 5.00 g of the polymer was then dissolved in 20 g of ethanol, yielding a 20% solution. Depending on the substance(s) added this or a more concentrated solution was used to make the spin-blends.

Sample 15. Poly HEMA (7.07 g) was placed into a beaker and 38.39 g of ethanol was added. The beaker was then heated to dissolve the polymer. Once the polymer began to go into solution 1.25 g of glycolic acid in 2.02 g of ethanol were added. The final solution contained 5.5% glycolic acid and 15% poly HEMA. Like previously mentioned solutions the substances added to the polymer helped to determine the polymer concentration in solution.

Sample 16. To make a PVP-$I_2$ solution, PVP (9.02 g of 360,000 MW) was dissolved in absolute ethanol. $I_2$ (1.04 g) was dissolved into 50 mL of absolute ethanol. The two were combined in a flask and heated in an oil bath at 50–90° C. at reflux for 3.5 hours. The solution was then subjected to vacuum to remove excess ethanol. The final solution was 17% polymer by weight.

The production of fibers with additional theraputic performance enhancing additives.

Sample 17. Lidocaine was put into ethanol to form a 23% solution and then added to the various polymer solutions to yield a 2.5% lidocaine concentration in the spun fibers.

Samples with lidocaine in them were then tested for lidocaine release. A sample of Example 1 and lidocaine were spun using 18 KV, 120 μamperes, and a gap distance of 26 cm. This solution yielded fibers with a diameter ranging from 400–700 nm. Example 6 and lidocaine were spun using 12 KV, 80 μamperes, and a gap distance of 30 cm. This solution yielded fibers with a diameter ranging from 1–5 μm.

Sample 18. Lidocaine was dissolved in ethanol and then placed in a petri dish with Waterlock 180. The ethanol was allowed to evaporate leaving the Waterlock coated in lidocaine. These particles were then added to polymer solutions and spun. The release study on these samples showed that the Waterlock slows down the release of the lidocaine from the nonwoven nanofiber mats. Example 1 and example 9 were spun using 21.0 KV at a gap distance of 20 cm. The fibers from this solution were 1 μm in diameter.

Sample 19. Erythromycin (0.10 g) was placed into 0.31 g of acetone and dissolved to form a 24% solution. The erythromycin solution was then added to a polymer solution. In the spun fibers the erythromycin had a concentration of 2.5% by weight. Example 1 and Example 10 were spun using 19.9 KV at a gap distance of 20 cm. The fibers from this solution were 1–2 μm in diameter.

Sample 20. Dextran was dissolved in distilled water and then added to a polymer solution. The typical dextran concentration was 4% by weight to polymer. Example 4 and example 11 were spun using 17.2 KV, 100 μamperes, and a gap distance of 20 cm. The fibers from this solution were 400–600 nm in diameter.

Sample 21. Most of the dyes that were spun with the PCL fibers were alcohol soluble. A 20–35% dye solution was made and then added to the polymer solution. The final concentration of dye in the spun fibers varied from 1.2% to 5.4%. Example 1 and example 12 were spun using 17 KV, 390 μamperes, and a gap distance of 23 cm. The fibers from this solution were 1–2 μm in diameter.

Sample 22. Adhesives were added to the polymer solutions and spun with the fibers. Rhoplex and oligomeric BE were both placed into solution and then tried in PCL fibers with limited success. Example 1 and example 13 were spun using 16.5 KV at a gap distance of 25 cm. The fibers from this solution were 1 μm in diameter.

Sample 23. Pluronic F-127 was dissolved in acetone and then added to the various polymer solutions. The Pluronic F-127 concentrations varied from 15–25% in the PCL samples. Example 1 and example 14 were spun using 17.5 KV, 30 μamperes, and a gap distance of 20 cm. The fibers from this solution were 1–2 μm in diameter.

Samples 24, 25, 26, 27, 28, and 29. Carbopol®, charcoal, Waterlock 180, chitosan and PEI-cellulose were all added as solids to form suspensions in the polymer solutions. Their concentrations varied widely based on the polymer solution concentration and the size of the particles. Example 1 and example 16 were spun using 21 KV, 21 μamperes, and a gap distance of 20 cm. The fibers from this solution were 1 μm in diameter. This solution did not suspend well. To help with the distribution of the particles a small electric drill with a 10 cm long glass-stirring rod, which was slightly bent at the one end was used to keep the particles suspended while the solution was spun.

A double-sided adhesive from Avery was used to attach the PCL fibers that were spun directly onto a human hand. A 1 cm thick ring of adhesive with a diameter of 3 cm was cut out of the Avery double-sided adhesive and placed on a human hand to allow fibers to affix to the surface of the skin.

Thus it should be evident that the dressing, device and methods of the present invention are highly effective in protecting and repairing wound surfaces. The invention is particularly suited for use to create thrombogenic dressings and for treating battlefield wounds, but is not necessarily limited thereto. The dressing, device and method of the present invention can be used separately with other equipment, methods and the like, as well as for the manufacture of other non-wound dressing materials.

Based upon the foregoing disclosure, it should now be apparent that the use of the dressing and device as described herein will carry out the objects set forth hereinabove.

It is, therefore, to be understood that any variations evident fall within the scope of the claimed invention and thus, the selection of specific component elements can be determined without departing from the spirit of the invention herein disclosed and described. In particular, the dressings produced according to the present invention are not necessarily limited to those achieved using the apparatus described. Thus, the scope of the invention shall include all modifications and variations that may fall within the scope of the attached claims.

What is claimed is:

1. An article of manufacture comprising:
   at least one fiber electrospun from a substantially homogeneous mixture containing at least one hydrophilic polymer, at least one polymer that is at least weakly hydrophobic and at least one pH adjusting compound.

2. The article of claim 1, wherein the article is a medical dressing.

3. The article of claim 2, wherein the substantially homogeneous mixture additionally contains at least one therapeutic performance enhancing additive.

4. The article of claim 3, wherein the at least one therapeutic performance enhancing additive is selected from the group consisting of antibiotic compounds, bacteriocidal compounds, fungicidal compounds, bacteriostatic compounds, crosslinking compounds, analgesic compounds, thrombogenic compounds, nitric oxide releasing compounds that promote wound healing, and nucleic acids.

5. The article of claim 4, wherein the at least one therapeutic performance enhancing additive is a nucleic acid selected from deoxyribonucleic acid, ribonucleic acid, and nucleotide analogs.

6. The article of claim 3, wherein the at least one hydrophilic polymer exhibits an equilibrium moisture content of greater than about 80 percent when spun as fibers of homopolymer.

7. The article of claim 3, wherein the at least one hydrophilic polymer is selected from the group consisting of linear poly(ethylenimine), grafted cellulosics, poly(ethyleneoxide), and poly vinylpyrrolidone, and the at least one polymer that is at least weakly hydrophobic is selected from The group consisting of polyesters and acrylics.

8. The article of claim 7, wherein the at least one hydrophilic polymer is linear poly(ethylenimine) and the at least one polymer that is at least weakly hydrophobic is poly(caprolactone).

9. The article of claim 2, additionally comprising an underlying double sided adhesive applied around the periphery of the dressing.

10. The article of claim 2, wherein the at least one fiber has a diameter of between about 3 nanometers and about 3000 nanometers.

11. The article of claim 10, wherein the at least one fiber has a diameter of between about 10 nanometers and about 500 nanometers.

12. The article of claim 11, wherein the at least one fiber has a diameter of between about 10 nanometers and about 100 nanometers.

13. The article of claim 2, having a surface area of at least about 5 m²/g.

14. The article of claim 2, wherein the pH adjusting compound is selected from carboxypolymerhylene, alginic acid, polyacrylic acid and derivatives thereof.

15. A method of producing at least one fiber comprising electrospinning a substantially homogeneous mixture comprising; a solvent, a polymer which is at least weakly hydrophobic, a hydrophilic polymer, and optionally, a pH adjusting component.

16. A method of using a medical dressing comprising:

applying fibers to a wound or other area needing protection from contamination or an area requiring treatment with therapeutical or pharmaceutical compounds, to form a fibrous non-woven matrix, wherein the fibers are electrospun from a substantially homogeneous mixture containing at least one hydrophilic polymer, and at least one polymer which is at least weakly hydrophobic, and optionally, a pH adjusting compound.

17. An apparatus for electrospinning at least one polymer fiber comprising:

at least one reservoir;

at least one device for electrospinning at least one fiber, the at least one device being in fluid communication with the at least one reservoir;

a mixing device for agitating the fluid within the reservoir;

a power source capable of generating an electric field in electrical communication with the at least one device; and a device for focusing the electrospun fibers into a defined area.

* * * * *

UNITED STATES PATENT AND TRADEMARK OFFICE
CERTIFICATE OF CORRECTION

PATENT NO. : 6,753,454 B1
DATED : June 22, 2004
INVENTOR(S) : Daniel J. Smith et al.

It is certified that error appears in the above-identified patent and that said Letters Patent is hereby corrected as shown below:

Column 21,
Line 26, "carboxypolymerhylene" should read -- carboxypolymethylene --.

Signed and Sealed this

Seventh Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,753,454 B1
DATED : June 22, 2004
INVENTOR(S) : Daniel J. Smith et al.

It is certified that error appears in the above-identified patent and that said Letters Patent is hereby corrected as shown below:

Title page,
Item [73], Assignee, should read -- The University of Akron, Akron, OH (US); The United States of America as Represented by the Secretary of Defense, Washington D.C. --.

Column 1,
Line 7, please insert the following:
-- The U.S. Government has a paid-up license in this invention and the right in limited circumstances to require the patent owner to license others on reasonble terms as provided for by the terms of Contract No. DAAH04-96-C-0086 awarded by Battelle, Columbus Division. --

Signed and Sealed this

Twenty-eighth Day of June, 2005

JON W. DUDAS
*Director of the United States Patent and Trademark Office*